United States Patent [19]

Berke et al.

[11] Patent Number: 5,304,213
[45] Date of Patent: Apr. 19, 1994

[54] HYPER-HYPOTHERMIA BLANKET WITH FILTRATION PROPERTIES

[75] Inventors: Leonard D. Berke; Michael C. Molloy, both of Cincinnati, Ohio

[73] Assignee: Cincinnati Sub-Zero Products, Inc., Cincinnati, Ohio

[21] Appl. No.: 75,362

[22] Filed: Jun. 14, 1993

[51] Int. Cl.$^5$ .............................................. A61F 7/00
[52] U.S. Cl. .................................... 607/104; 607/114
[58] Field of Search ............................ 128/399–400, 128/402–403; 607/96, 104, 108–112, 114

[56] References Cited

U.S. PATENT DOCUMENTS

| | | |
|---|---|---|
| 2,093,834 | 9/1937 | Gaugler . |
| 2,601,189 | 6/1952 | Wales, Jr. . |
| 2,991,627 | 7/1961 | Suits . |
| 3,867,939 | 2/1975 | Moore et al. . |
| 4,540,412 | 9/1985 | Van Overloop ............... 128/399 X |
| 4,572,188 | 2/1986 | Augustine et al. . |
| 4,660,388 | 4/1987 | Greene, Jr. . |
| 4,777,802 | 10/1988 | Feher . |
| 5,125,238 | 6/1992 | Ragan et al. . |
| 5,168,589 | 12/1992 | Stroh et al. . |
| 5,184,612 | 2/1993 | Augustine . |

Primary Examiner—Angela D. Sykes
Attorney, Agent, or Firm—Charles R. Wilson

[57] ABSTRACT

A hyper-hypothermia disposable blanket for use by medical personnel warms or cools a patient by a stratum of temperature controlled and filtered air. The blanket comprises a bottom layer of air pervious non-woven material and a top layer of air impervious material. The top layer is sealed at its edges to the bottom layer to form a chamber therebetween. A set of longitudinal seals within the chamber is used to create air flow channels and a manifold. A receptacle opening is also provided in the top layer near a foot end to detachably receive an air hose such that temperature controlled air passes into the manifold and is then directed to flow primarily through outermost air flow channels and eventually into an innermost air flow channel. The air flow creates a build up of pressurized air in the chamber which ultimately causes a stratum of air having a substantially uniform temperature to flow through the bottom layer of the blanket and onto the patient. The air which contacts the patient is filtered and is substantially uniform temperatured air because of the air flow channels and nature of the air pervious material.

18 Claims, 3 Drawing Sheets

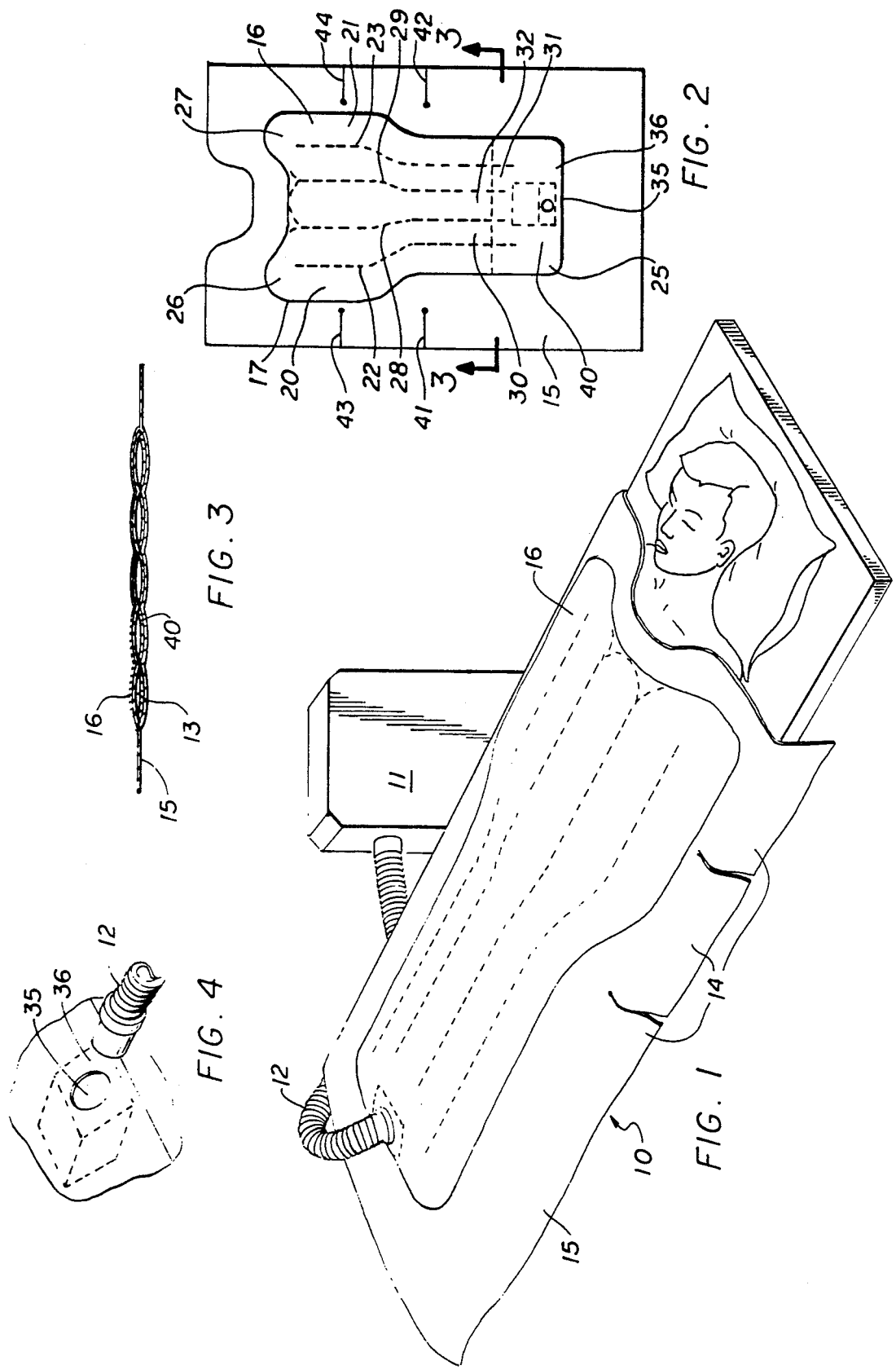

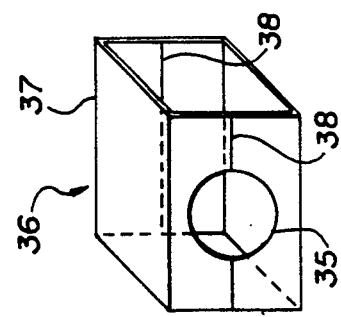
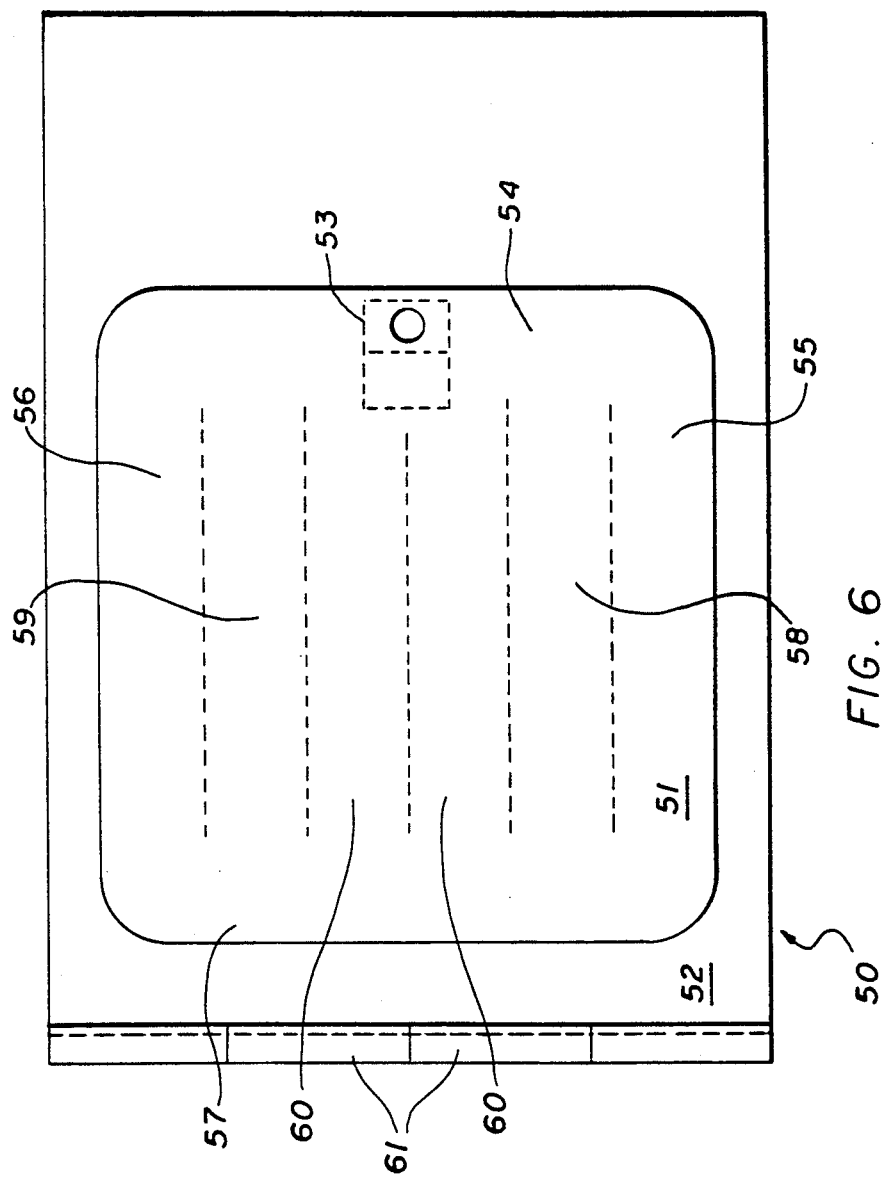
FIG. 5
FIG. 6

HYPER-HYPOTHERMIA BLANKET WITH FILTRATION PROPERTIES

This invention relates to a hyper-hypothermia blanket. More particularly, the invention relates to a disposable hyper-hypothermia blanket for use with a heat or cooling source to supply controlled temperature air in a substantially even flow pattern to a patient.

Hypothermia is a condition experienced by warm blooded animals after some abnormal event. A life threatening extreme condition occurs when an individual has had prolonged exposure to a hostile environment such as freezing rain, snow or bitter cold. A hospital patient who is undergoing or has just undergone a medical procedure is also prone to experience hypothermia. Influencing factors for hypothermia in these patients include the loss of body heat due to body exposure during pre-operation prepping, cold operating room temperatures, breathing of dry anesthetic gases, adverse effects of anesthesia on body temperature regulation, evaporation of moisture from exposed organs during the operation and cold intravenous fluids.

Regardless of the cause of hypothermia, the individual initially experiences extreme discomfort. The discomfort can quickly lead to a life threatening situation. Anyone suffering from hypothermia should be attended to so as to avoid irreversible body temperature drop or even death. An obvious cure to the problem is to raise the body temperature of the individual. Simply wrapping a person suffering from hypothermia in a blanket is a solution which can provide some relief. The effect of the blanket is to retain body heat. This results in a gradual warming of the body. However, there are times when a blanket alone will not suffice. The ability of the body to produce sufficient heat in sufficient time may not be possible or feasible in certain situations. Additionally, use of a blanket during or after an operation in a hospital can be cumbersome. It may be difficult to fully cover the patient's body due to intravenous tubing and other life supporting equipment which physically hinders placement of the blanket.

An individual also experiences discomfort with an elevated body temperature. An abnormally high body temperature can be caused internally such as by a virus or externally such as by inclement weather as encountered in the summer. Regardless of the cause, the individual suffering from a hyperthermia condition also wants immediate relief. Cold water baths and wet towel compresses provide immediate relief. In extreme cases where a quicker body temperature lowering is needed, ice water baths and ice compresses are applied to the individual. While effective, cold water baths have attendant problems. The individual is inconvenienced and after a length of time the cold water itself is damaging to the skin. The wet towel and ice compress treatments also are effective, though require continued changing. The aforementioned problems are exacerbated when the individual being treated is ill, possibly even to the extent that nursing personnel must administer the treatment.

Various articles have been developed for use specifically on victims suffering from hypothermia and also victims suffering from hyperthermia. Such articles are specially constructed for use by professionally trained individuals. Specially constructed blankets are capable of having a fluid circulating through tubes embedded in the blanket. The temperature of the fluid in the blanket is controlled by an external source.

There also have been devised various articles which control the patient's body temperature by directing temperature controlled air to the surface of the body. Thus, there are articles which are dimensioned to overlie the patient's body much as a blanket does. Air is directed into the article and through holes in the article so as to contact the body. Examples of such articles are found in U.S. Pat. Nos. 2,110,022, 2,601,189, 4,572,188, 4,660,388, 4,777,802, 4,867,230, 5,097,548, 5,125,238 and 5,184,612. Articles of the prior art are deficient in one or more ways; for example, heat retention effectiveness, cost of construction, strength of materials, bulkiness, and ease of use.

A particular concern with the known prior art articles is that a slow steady flow of warmed or cooled air onto the patient at the approximate same temperature throughout is not always provided. Rather, forced air currents emanating from the article are often strong. There is a consequent concern for carrying air borne contaminants into direct contact with an open wound or surgical incision on the patient. Bacteria in the air can also be carried by the air currents to such sensitive areas and cause infections. Of lesser concern, though still important is the fact that localized hot and cold spots are sometimes formed which can be potentially damaging to the skin of the patient.

There has now been developed a convective hyper-hypothermia blanket primarily for use by hospital personnel to treat patients. The hyper-hypothermia blanket is constructed in a manner which effectively provides filtered air of substantially uniform temperature to the patient,s body surface without the use of strong air currents. The construction of the blanket is such that it is economical to produce, easy to use and provides various features deemed necessary or desirable by medical professionals.

SUMMARY OF THE INVENTION

A light-weight disposable convective hyper-hypothermia blanket is constructed to deliver temperature controlled filtered air to a patient's body. The blanket comprises a bottom layer of an air pervious material and a top layer of an air impervious material. The top layer is sealed at its edges to the bottom layer to form an air receiving chamber and peripheral drape sections. The top layer is also selectively sealed to the bottom layer to create at least three longitudinal air flow channels running substantially the length of the chamber and a manifold within the chamber at one end thereof. A receptacle opening is provided in the blanket to detachably receive an air hose from a heat generating unit or air cooling unit. Heated or cooled air is received into the manifold where it is directed into the outermost air flow channels and ultimately into the innermost air flow channel. A build up of pressure occurs until the air is forced through the bottom layer as a stratum of substantially uniform temperatured air and onto the patient. The air pervious material is capable of filtering the air and acting as a bacteria barrier as the air passes through it.

BRIEF DESCRIPTION OF THE DRAWINGS

FIG. 1 is a schematic view in perspective of the convective hyper-hypothermia blanket of this invention positioned for use.

FIG. 2 is a top view of the hyper-hypothermia blanket of FIG. 1.

FIG. 3 is a partial view in section of the hyper-hypothermia blanket taken along line 3—3 of FIG. 2.

FIG. 4 is a partial perspective view in detail of the hyper-hypothermia blanket of FIG. 1 showing a receptacle opening for receiving an air hose.

FIG. 5 is a perspective view of a reinforcing collar used in conjunction with the hyper-hypothermia blanket's receptacle opening to receive the air hose and direct the flow of air.

FIG. 6 is a top view of a hyper-hypothermia blanket of the invention dimensioned for use on a lower body area of a patient.

DETAILED DESCRIPTION OF THE INVENTION

Figure 7:
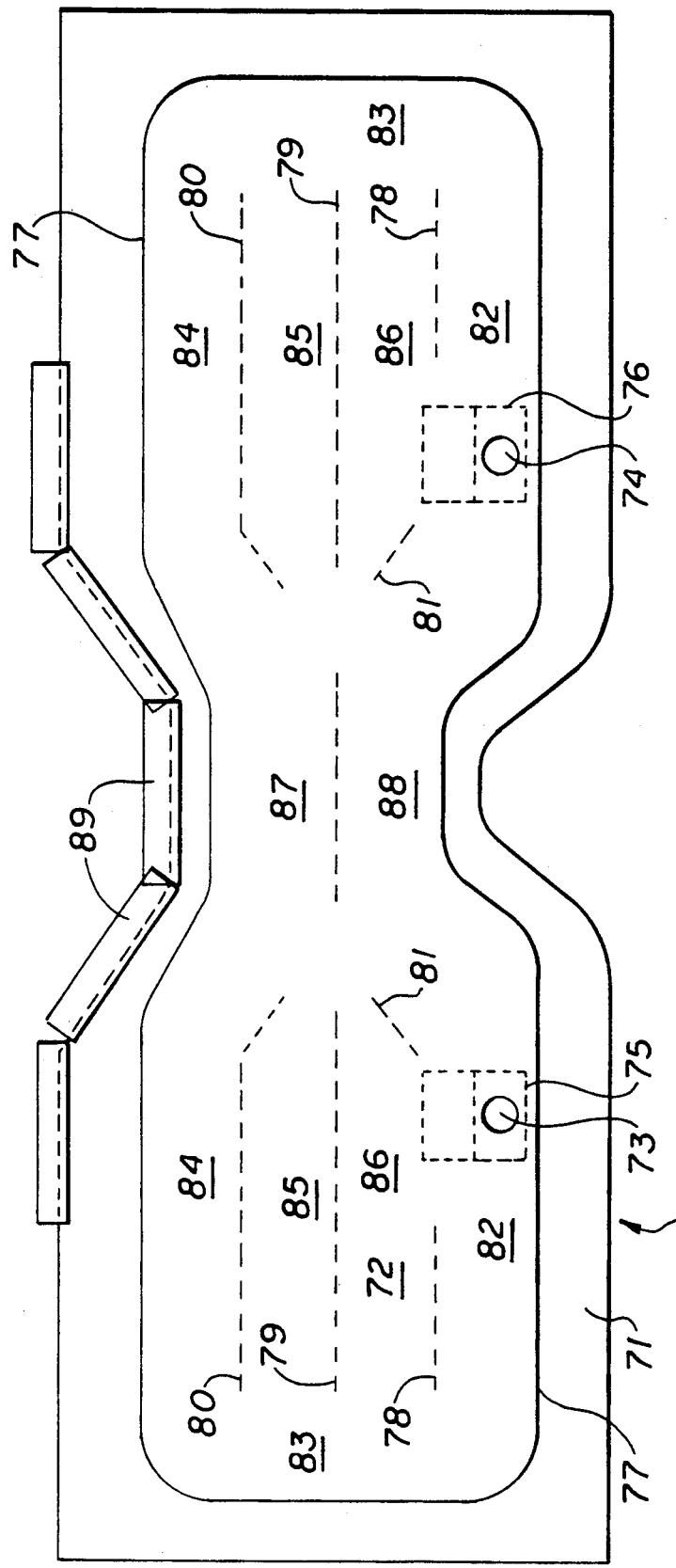
FIG. 7 is a top view of a hyper-hypothermia blanket of the invention dimensioned for use on an upper body area of a patient.

The convective hyper-hypothermia blanket of this invention is described in detail in the following paragraphs. While the blanket is described with particular reference to the drawings, it should be understood that other variations of the invention are possible. The blanket is useful with patients suffering or prone to a hypothermia condition or a hyperthermia condition. However, the hyper-hypothermia blanket is especially useful for providing heated air to a patient suffering with hypothermia and, for this reason, such use is described in the following paragraphs.

With reference to FIG. 1, there is shown a convective hyper-hypothermia blanket 10 positioned over a patient to provide a full cover. The blanket 10 is operably connected to a heat source 11 by means of an air delivery hose 12. The heat source 11 is a conventional electric resistance heater with thermostat controls to supply a source of heated air to an outlet. A fan built into the heat source forces the heated air through the outlet and into the delivery hose 12. Heat sources of this general nature are well known and are commercially available. Most are electric resistance heaters with sensitive thermostat means to control the temperature of the air. Various monitoring means and safety shut-off means are typically built into such heat sources especially when intended for use in a medical facility. Air cooling units which are substituted for the heat generating unit to alleviate a hyperthermia condition are also well known and are similarly provided with needed thermostat means.

The convective hyper-hypothermia blanket 10 as best seen in FIGS. 1-3 is formed from two joined together in a manner to form an air receiving chamber 13 therebetween and peripheral drape sections 14. A bottom layer 15 is a substantially air pervious material. It is a non-woven material capable of filtering heated air which is forced through it. Air borne contaminants are removed from the air stream by the filtering action of the material. Additionally, it is a barrier to the flow of bacteria. Interstices in the non-woven material are sufficiently small that the air borne contaminates and bacteria are physically prevented from passing. Such materials are known and are commercially available. The top layer 16 is an air impervious material which in effect as discussed below causes pressurized air in the air chamber 13 between the two layers to flow through the bottom layer 15. The top layer preferably has a layer or coating of a polymeric material such as polyethylene or polypropylene to enhance the air imperviousness of the layer. Preferably, the polymeric material is on the inside surface of the layer to enhance its sealing capability for the reasons which follow. Materials used to make the top layer are as well commercially available. Nonwoven fabrics of natural or synthetic fibers or cellulosic are used. The materials are sufficiently flexible that the blanket can be folded during shipping and storage for convenience purposes.

The blanket 10 is dimensioned to overlie a patient's body and is intended to extend from foot to neck and from side to side. Preferably, the blanket 10 depicted in FIGS. 1 and 2 is dimensioned to completely overlie a patient's body. For an adult patient, the blanket ranges from about seven feet to about eight feet in length and from about four feet to about six feet in width. The blanket 10 is generally rectangular-shaped with a centered cut-out at a head end to better accommodate the head of the patient. However, the dimensions of the blanket are not critical and depend primarily on the perceived needs of personnel using it. In particular, smaller versions of the blanket are contemplated for use with children and also for use to cover only a portion of the body, e.g. the legs and lower torso or the arms and upper torso as illustrated in FIGS. 6 and 7, respectively and as discussed below.

As best seen in FIG. 2, the bottom and top layers of material are sealed together at selected areas. The top layer 16 is smaller than the bottom layer 15. It is initially positioned in a mid-section of the bottom layer such that the drape sections 14 are created around the periphery of the blanket. Preferably, the top layer is torso-shaped and is centered in a mid-section of the bottom layer to create peripheral drape sections of about equal depth. The top layer is sealed at its edges 17 to the bottom layer to create the air receiving chamber 13. A heat seal is most conveniently used, though an adhesive seal or any other type seal can be used.

The blanket's top layer also has internal seals to its bottom layer to create air flow channels and a manifold within the air receiving chamber. Two outermost air flow channels 20 and 21 are created, each of which extends along one side of the chamber. Seals 22 and 23 defining these air flow channels extend from near the foot end of the blanket to near the head end of the blanket. They do not extend fully to a peripheral seal, but rather stop short of the peripheral seals so that a manifold 25 and cross flow channels 26 and 27 are created. Two intermediate seals 28 and 29 are used to create intermediate air flow channels 30 and 31 and an innermost air flow channel 32 in the blanket 10. Thus, each of these intermediate seals extend from the peripheral seal at the head end to near the foot end. The manifold 25 within the chamber is the area near the foot end from the seals' terminuses to the peripheral seal. As explained below, the internal seals are such that heated air forced into the chamber is caused to primarily first flow through the two outermost air flow channels 20 and 21, into the two intermediate air flow channels 30 and 31 and finally into the innermost air flow channel 32.

A receptacle opening 35 is positioned in the approximate center of the top layer near the foot end of the blanket 10 for the purpose of receiving the air delivery hose 12 from the heat source 11. The opening is shaped to match the end portion of the air delivery hose in a sealing fashion. A semi-rigid reinforcing collar 36 is interposed in the top layer and includes the opening.

The collar serves to better hold and retain the air delivery hose and to direct the heated air laterally through the manifold towards the outermost air flow channels. As best seen in FIG. 5, the collar 36 preferably has a collapsible box-like design which allows it to fold down upon itself. This feature allows the collar to flatten and the blanket to be readily folded and packaged in a compact container. Thus, the collar 36 is an open-ended box member 37 with a center horizontal fold line 38 on two opposite walls extending from outer peripheries of the box member to facilitate the collapsing of the collar. The semi-rigid nature of the collar ensures that the flexible walls of the blanket will not collapse or partially fold at the receptacle opening area to impede the flow of air to the hollow interior. The open ends of the box member 37 direct air laterally.

With reference to FIG. 2, an insulating liner 40 shown in phantom is secured to the bottom layer 15 within the manifold 25 of the air chamber formed by the bottom and top layers. The insulating liner ensures that excessive heat which may be present at the point where the heated air first enters the chamber is not transferred to the patient's feet. Rather, the heated air is caused to flow throughout the chamber and in effect its temperature is evened out before being transferred into direct contact with the patient. The insulating liner is a synthetic polymeric sheet which is impermeable to air. Other liners such as fabric can be used, though are less preferred because of the special steps needed to secure them in place.

Heated air from the heat source first enters the manifold 25 of the hyper-hypothermia blanket's air receiving chamber through the receptacle opening 35. The open-ended box member 37 of the collar 36 directs the heated air laterally through the manifold 25 and into the outermost air flow channels 20 and 21. Continued forcing of the heated air into the air receiving chamber forces it to then flow into the intermediate air flow channels 30 and 31 and finally into the innermost air flow chamber 32. The air chamber becomes filled with the heated air and initially a build up of pressure occurs. This pressure will be substantially constant throughout the air receiving chamber because of the unobstructed air flow channels and free flow of air throughout. Once the pressure because sufficiently great enough, air will be forced through the bottom layer because of its air pervious nature. The air which exits the chamber does so as a continuous stratum of substantially uniform temperatured air. There are no air currents, rather a bath of heated and filtered air contacts the patient.

With reference to FIG. 2, optionally, a series of slits are added to the blanket to enhance its use by medical personnel. The slits are in the bottom layer of the blanket and create separate drape sections. The slits extend from an edge of the bottom layer 15 in towards the center of the blanket up to the top layer 16. As shown, slits 41 and 42 extend from the approximate mid-length of the blanket on each side. Slits 43 and 44 extend from the approximate one-fourth length from the head end of the blanket on each side. The slits facilitate a flipping back of a drape section of the blanket so that the patient can be attended to without exposing the full body of the patient and losing all benefit of the heat retention characteristics of the blanket.

FIGS. 6 and 7 show alternative hyper-hypothermia blankets of the invention which are not full cover blankets. The blanket 50 illustrated in FIG. 6 is intended to cover the lower part of the patient's body, primarily the feet, legs and lower torso. It is dimensioned accordingly. The blanket has an air receiving chamber and drape sections formed by sealing the edges of the top layer 51 of air impervious material to the bottom layer 52 of air pervious material. Internal longitudinal seals are provided to create six air flow channels, a cross flow channel and a manifold within the air chamber. A reinforcing collar 53 is positioned in the foot end of the blanket. A set of adhesive tape segments 61 extend across the end opposite the foot end for the purpose of holding the blanket 50 in place during use. Similar in operation to the blanket 10 illustrated in FIGS. 1-4, temperature controlled air flows through a receptacle opening in the reinforcing collar 53 into the manifold 54 and is directed primarily to the outermost air flow channels 55 and 56. The air then flows through the cross flow channel 5 into the intermediate air flow channels 58 and 59 and finally into the two innermost flow channels 60. Eventually, a build up of air pressure in the air chamber causes a stratum of temperature controlled and filtered air through the bottom layer and onto the patient.

The hyper-hypothermia blanket 70 illustrated in FIG. 7 is intended for use on the patient's upper torso and arms. The blanket 70 has a main body and two wings and is dimensioned such that it can be used when the patient's arms are fully outstretched. The blanket has a bottom layer 71 of air pervious material and a top layer 72 of air impervious material sealed together to form an air receiving chamber and drape sections. The top layer is sealed at its edges and has internal seals to create longitudinal air flow channels and at least one manifold. As shown, the blanket has two receptacle openings 73 and 74. An opening is provided on both sides of the blanket for convenience of use by medical personnel. Each has a pull-seal label closing off the openings, one of which can simply be removed when the blanket is ready for use. A thin non-sealing membrane covering which is easily broken can also be used. The collars 75 and 76 in the receptacle openings are similar in construction to that described with reference to FIG. 5. The seal 77 on the edges of the top layer 72 creates an air receiving chamber between the top layer and the bottom layer. Longitudinally running internal seals 78, 79 and 80 on each side of the blanket create air flow channels. The aforementioned internal seals are substantially equi-spaced. Internal guide seals 81 are positioned near the blanket's main body. A seals 78 and 81 create a manifold 82 for directing the heated air laterally as it is first received through one of the openings 73 or 74. The internal seals create the manifold 82, a cross flow channel 83, an outermost air flow channel 84 and innermost air flow channels 85 and 86 on each wing of the blanket and cross-over channels 87 and 88 in the main body. Tape segments 89 which extend partially across an outer edge of the blanket opposite the receptacle openings are used to hold the blanket 70 in place during use.

Air which flows through the opening 73 or 74 of the blanket 70 into the manifold 82 flows primarily first into the cross flow channel 83 and cross-over channel 88, outermost air flow channels 84 and ultimately into innermost air flow channels 85 and 86 until the air chamber fills with pressurized temperature controlled air. It then is forced through the bottom layer as a stratum and onto the patient in a manner as above described with reference to the blanket 10 of FIGS. 1-5. The blanket,s full size need not be used. It can be fold at one or both outer portions such that only the torso of the patient receives the air.

In operation, the full cover embodiment of the convective hyper-hypothermia blanket of the invention is positioned over a patient who shows symptoms of hypothermia or hyperthermia. The end with the air hose receptacle opening is placed near the patient's feet with the blanket itself extending substantially along the patient's body to near his head. If needed, portions of the blanket are folded over so as to effectively shorten the overall length or width. Next, the air delivery hose is inserted into the blanket's receptacle opening. The temperature control of the heat or cooling source is set to a desired setting and the source activated. Temperature controlled air flows through the delivery hose and into the hyper-hypothermia blanket. The blanket is filled with the air, whereupon the air then passes through the air pervious bottom layer and onto the patient. Air flow through the air pervious bottom layer is substantially even. That is, because of the forced air flow and the degree of air permeability of the bottom layer, the temperature controlled air directed into the chamber of the blanket quickly builds up a pressure throughout and is ultimately forced through the air pervious bottom layer as a substantially uniform temperature stratum. There are no hot spots or cool areas. When the patient's body temperature returns to normal, the blanket is removed and discarded. The partial cover blankets of the invention are used in the same manner and operate the same.

While the invention has been described in detail with reference to the drawings, it should be understood other variations and modifications are possible. All such changes of an obvious nature are considered within the scope of the following claims.

I claim:

1. A light-weight disposable convective hyper-hypothermia blanket for use in controlling a patient's body temperature whereby a substantially uniform temperature stratum of air is forced onto the patient, said blanket comprising:

(a) a bottom layer of air pervious non-woven material which filters air as it passes therethrough and acts as a bacteria barrier, said bottom layer of air pervious material dimensioned to overlie at least a portion of the patient's body;

(b) a top layer of air impervious material overlying the bottom layer of air pervious material and sealed at its edges thereto to form an air receiving chamber from which said air is forced onto the patient, further wherein the top layer of air impervious material is selectively sealed to the bottom layer to form at least three longitudinal air flow channels comprising outermost air flow channels and an innermost air flow channel, the air channels running substantially the length of the chamber and to form a manifold within the chamber at one end thereof; and (c) a reinforcing collar with a receptacle opening in the top layer of air impervious material to detachably receive an air hose from a heat or cooling source, said receptacle opening positioned centrally and in communication with the manifold of the chamber whereby temperature controlled air from the heat or cooling source is initially directed into the manifold of the chamber and then directed primarily to the outermost air flow channels and then to the innermost air flow channel such that a build up of pressurized controlled temperature air within the chamber occurs until the pressurized air is forced through the bottom layer of air pervious material as the substantially uniform temperatured stratum of air onto the patient.

2. The hyper-hypothermia blanket of claim 1 wherein the reinforcing collar is an open-ended box member, the receptacle opening being in one side wall of the box member and open ends of the box member being positioned such that controlled temperature air is forced through said open ends and into the outermost air flow channels.

3. The hyper-hypothermia blanket of claim 2 wherein the reinforcing collar has center-line fold lines on two opposite side walls to facilitate a collapsing of the collar to a flattened state for ease of convenience in folding and storing the blanket when in non-use.

4. The hyper-hypothermia blanket of claim 3 wherein the blanket is generally rectangular-shaped with a foot end and a head end and wherein the receptacle opening is in the foot end.

5. The hyper-hypothermia blanket of claim 4 wherein the blanket dimensioned to fully cover the patient.

6. The hyper-hypothermia blanket of claim 5 wherein the top layer of air impervious material is torso-shaped.

7. The hyper-hypothermia blanket of claim 4 wherein the blanket is dimensioned to cover a lower body area of the patient.

8. The hyper-hypothermia blanket of claim 7 further comprising a set of adhesive tape segments extending across the end opposite the end having the receptacle opening for holding the blanket in place during use.

9. The hyper-hypothermia blanket of claim 4 wherein the top layer is selectively sealed to the bottom layer to create two outermost air flow channels, two intermediate air flow channels and an innermost air flow channel.

10. The hyper-hypothermia blanket of claim 9 wherein each outermost air flow channel and an adjoining intermediate air flow channel are formed by an internal seal which runs from near the foot end of the blanket to near the head end of the blanket and each intermediate air flow channel and adjoining said innermost air flow channel are formed by an internal seal which runs from a peripheral seal at the head end to near the foot end.

11. The hyper-hypothermia blanket of claim 4 wherein an insulating liner is positioned in the manifold to reduce the transfer of air to the feet of the patient.

12. The hyper-hypothermia blanket of claim 1 wherein the blanket is dimensioned to cover an upper body area and outstretched arms of the patient.

13. The hyper-hypothermia blanket of claim 12 further comprising a set of adhesive tape segments extending across an end of the blanket opposite the receptacle opening for holding the blanket in place during use.

14. A light-weight disposable convective hyper-hypothermia blanket for use in controlling a patient's body temperature whereby a substantially uniform temperatured stratum of air is forced onto the patient, said blanket comprising:

(a) a bottom layer of air pervious non-woven material which filters air as it passes therethrough and acts as a bacteria barrier, said bottom layer of air pervious material dimensioned to overlie at least a portion of the patient's body;

(b) a top layer of air impervious material overlying the bottom layer of air pervious material and sealed at its edges thereto to form an air receiving chamber from which said air is forced onto the patient, further wherein the top layer of air impervious material is selectively sealed to the bottom layer to form (i) longitudinal air flow channels comprising outermost air flow channels, intermediate air flow channels and innermost air flow channels wherein the air channels all run substantially the length of the chamber, (ii) a manifold within the chamber at a foot end thereof and (iii) a cross flow channel at a head end thereof opposite the foot end; and (c) a reinforcing collar with a receptacle opening in the top layer of air impervious material to detachably receive an air hose from a heat or cooling source, said receptacle opening positioned centrally and in communication with the manifold of the chamber whereby temperature controlled air from the heat or cooling source is initially directed into the manifold of the chamber and then directed primarily to the outermost air flow channels and cross flow channel, then to the intermediate air flow channels and the innermost air flow channels such that a build up of pressurized controlled temperature air within the chamber occurs until the pressurized air is forced through the bottom layer of air pervious material as the substantially uniform stratum of air onto the patient.

15. The hyper-hypothermia blanket of claim 14 wherein the reinforcing collar is an open-ended box member, the receptacle opening being in one side wall of the box member and open ends of the box member are positioned such that controlled temperature air is forced through said open ends and into the outermost air flow channels.

16. The hyper-hypothermia blanket of claim 15 wherein the longitudinal air flow channels are formed by internal seals which run from near the foot end of the blanket to near the head end of the blanket.

17. A light-weight disposable convective hyper-hypothermia blanket for use in controlling a patient's body temperature whereby a substantially uniform temperatured stratum of air is forced onto the patient, said blanket comprising:

(a) a bottom layer of air pervious non-woven material which filters air as it passes therethrough and acts as a bacteria barrier, said bottom layer of air pervious material dimensioned to overlie an upper body area and outstretched arms of the patient's body;

(b) a top layer of air impervious material overlying the bottom layer of air pervious material and sealed at its edges thereto to form an air receiving chamber from which said air is forced onto the patient, further wherein the top layer of air impervious material is selectively sealed to the bottom layer to form at least three longitudinal air flow channels comprising outermost air flow channels and innermost air flow channels, the air channels running substantially the length of the chamber and to form a manifold within the chamber at one end thereof; and (c) a reinforcing collar with a receptacle opening in the top layer of air impervious material to detachably receive an air hose from a heat or cooling source, said receptacle opening in communication with the manifold of the chamber whereby temperature controlled air from the heat or cooling source is initially directed into the manifold of the chamber and then directed primarily to the outermost air flow channels and then to the innermost air flow channels such that a build up of pressurized controlled temperature air within the chamber occurs until the pressurized air is forced through the bottom layer of air pervious material as the substantially uniform temperatured stratum of air onto the patient.

18. The hyper-hypothermia blanket of claim 17 further comprising a set of adhesive tape segments extending across an end of the blanket opposite the receptacle opening, said tape segments holding the blanket in place during use.

* * * * *